(12) United States Patent
Yamauchi et al.

(10) Patent No.: US 12,098,137 B2
(45) Date of Patent: Sep. 24, 2024

(54) METHOD FOR MANUFACTURING CYCLOPROPANE COMPOUND

(71) Applicant: SUMITOMO CHEMICAL COMPANY, LIMITED, Chuo-ku (JP)

(72) Inventors: Kazuhiro Yamauchi, Osaka (JP); Junichi Tomokawa, Osaka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 686 days.

(21) Appl. No.: 17/274,059

(22) PCT Filed: Sep. 5, 2019

(86) PCT No.: PCT/JP2019/034882
§ 371 (c)(1),
(2) Date: Mar. 5, 2021

(87) PCT Pub. No.: WO2020/050339
PCT Pub. Date: Mar. 12, 2020

(65) Prior Publication Data
US 2021/0347759 A1  Nov. 11, 2021

(30) Foreign Application Priority Data
Sep. 7, 2018 (JP) ................. 2018-167925

(51) Int. Cl.
*C07D 401/12* (2006.01)
*C07C 51/09* (2006.01)
(Continued)

(52) U.S. Cl.
CPC ............ *C07D 401/12* (2013.01); *C07C 51/09* (2013.01); *C07C 51/412* (2013.01); *C07C 61/40* (2013.01);
(Continued)

(58) Field of Classification Search
CPC .................................................. C07D 401/12
(Continued)

(56) References Cited

U.S. PATENT DOCUMENTS

| 2012/0101105 A1 | 4/2012 | Inoue et al. |
| 2012/0165339 A1 | 6/2012 | Terauchi et al. |

(Continued)

FOREIGN PATENT DOCUMENTS

| CN | 105130957 A | 12/2015 |
| JP | 2015-509939 A | 4/2015 |

(Continued)

OTHER PUBLICATIONS

Clemenceau et al., Journal of the American Chemical Society (2020), 142(36), 15355-15361.*

Xue Xu et al., "Highly Asymmetric Intramolecular Cyclopropanation of Acceptor-Substituted Diazoacetates by Co(II)-Based Metalloradical Catalysis: Iterative Approach for Development of New-Generation Catalysts", Journal of the American Chemical Society, 2011, 133, pp. 15292-15295.

Pan Li et al., "Iodine-catalyzed diazo activation to access radical reactivity", Nature Communications, (2018) 9:1972, pp. 1-9.

International Search Report issued on Dec. 10, 2019 in PCT/JP2019/034882 filed on Sep. 5, 2019, 3 pages.

(Continued)

*Primary Examiner* — Niloofar Rahmani
(74) *Attorney, Agent, or Firm* — Oblon, McClelland, Maier & Neustadt, L.L.P.

(57) ABSTRACT

The present invention provides an industrially advantageous production method of (1R,2S)-2-{[((2,4-dimethylpyrimidin-5-yl)oxy}methyl]-2-(3-fluorophenyl)-N-(5-fluoropyridin-2-yl)cyclopropane-1-carboxamide.

(1R,2S)-2-{[((2,4-Dimethylpyrimidin-5-yl)oxy}methyl]-2-(3-fluorophenyl)-N-(5-fluoropyridin-2-yl)cyclopropane-1-carboxamide (compound [A]) is produced by an industrially advantageous method by a route via a novel compound.

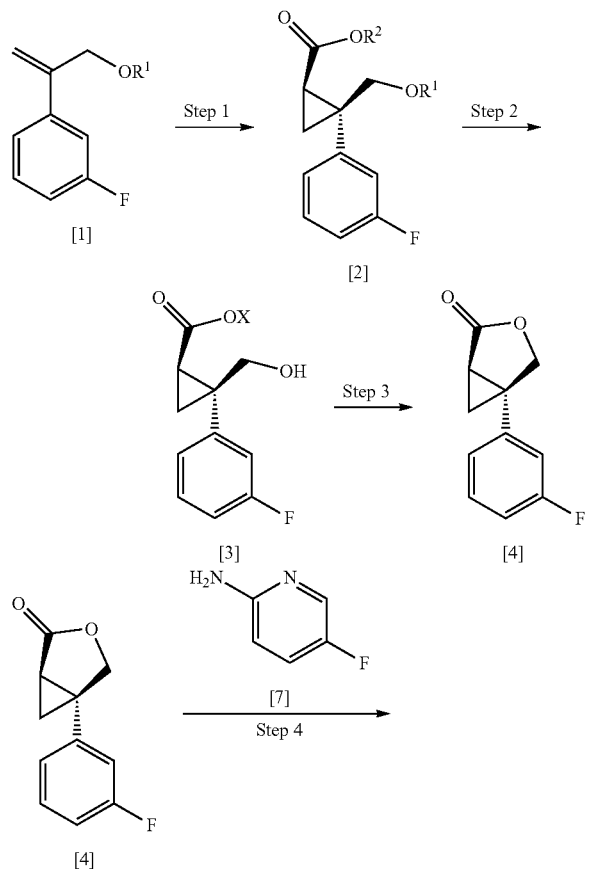

(Continued)

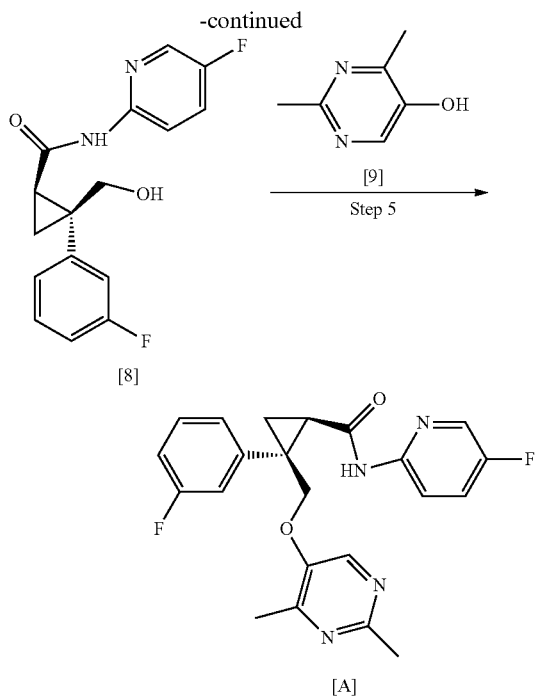

wherein each symbol is as described in the description.

6 Claims, No Drawings

(51) Int. Cl.
    *C07C 51/41* (2006.01)
    *C07C 61/40* (2006.01)
    *C07C 67/035* (2006.01)
    *C07C 67/347* (2006.01)
    *C07C 303/26* (2006.01)
    *C07C 309/66* (2006.01)
    *C07D 213/75* (2006.01)
    *C07D 307/93* (2006.01)

(52) U.S. Cl.
    CPC .......... *C07C 67/035* (2013.01); *C07C 67/347* (2013.01); *C07C 303/26* (2013.01); *C07C 309/66* (2013.01); *C07D 213/75* (2013.01); *C07D 307/93* (2013.01); *C07B 2200/07* (2013.01); *C07C 2601/02* (2017.05)

(58) Field of Classification Search
    USPC .......................................................... 544/298
    See application file for complete search history.

(56) References Cited

U.S. PATENT DOCUMENTS

| | | |
|---|---|---|
| 2014/0242647 A1 | 8/2014 | Coelho et al. |
| 2015/0025237 A1 | 1/2015 | Moniz et al. |
| 2015/0322052 A1 | 11/2015 | Inoue et al. |
| 2016/0032330 A1 | 2/2016 | Renata et al. |
| 2016/0318858 A1 | 11/2016 | Moniz et al. |
| 2018/0044285 A1 | 2/2018 | Moniz et al. |
| 2019/0076542 A1 | 3/2019 | Phillips et al. |
| 2022/0313826 A1 | 10/2022 | Phillips et al. |

FOREIGN PATENT DOCUMENTS

| | | |
|---|---|---|
| JP | 6147279 B2 | 6/2017 |
| WO | WO 2017/197046 A1 | 11/2017 |

OTHER PUBLICATIONS

Yoshida, Y. et al., "Discovery of (1R,2S)-2-{[(2,4-Dimethylpyrimidin-5-yl)oxy]methyl}-2-(3-fluorophenyl)-N-(5-fluoropyridin-2-yl)cyclopropanecarboxamide(E2006): A Potent and Efficacious Oral Orexin Receptor Antagonist," Journal of Medicinal Chemistry, vol. 58, 2015, p. 4648-4664.

Ol, N. et al., "Synthesis and Evaluation of Novel Radioligands for Positron Emission Tomography Imaging of the Orexin-2 Receptor," Journal of Medicinal Chemistry, vol. 56, 2013, p. 6371-6385.

\* cited by examiner

METHOD FOR MANUFACTURING CYCLOPROPANE COMPOUND

TECHNICAL FIELD

The present invention relates to a production method of cyclopropane compounds.

BACKGROUND ART

As a therapeutic agent for sleep disorders such as insomnia, the following (1R,2S)-2-{[((2,4-dimethylpyrimidin-5-yl)oxy}methyl]-2-(3-fluorophenyl)-N-(5-fluoropyridin-2-yl)cyclopropane-1-carboxamide is known (Patent Document 1).

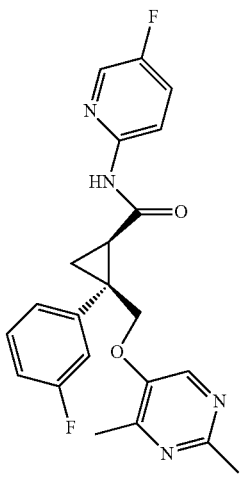 [SMILES: Cc1ncc(OC[C@@]2(c3cccc(F)c3)C[C@H]2C(=O)Nc2ccc(F)cn2)c(C)n1]

Moreover, Patent Document 1 discloses that the above compound is produced in 10 steps from 3-fluorophenylacetonitrile and an expensive optical isomer (R)-epichlorohydrin, as starting materials.

DOCUMENT LIST

Patent Document

[Patent Document 1] JP 6147279 B2

SUMMARY OF THE INVENTION

Problems to be Solved by the Invention

The present invention aims to provide an industrially advantageous production method of (1R,2S)-2-{[((2,4-dimethylpyrimidin-5-yl)oxy}methyl]-2-(3-fluorophenyl)-N-(5-fluoropyridin-2-yl)cyclopropane-1-carboxamide.

Means of Solving the Problems

The present inventors have conducted intensive studies in an attempt to solve the above-mentioned problem, and have found that the objective (1R,2S)-2-{[((2,4-dimethylpyrimidin-5-yl)oxy}methyl]-2-(3-fluorophenyl)-N-(5-fluoropyridin-2-yl)cyclopropane-1-carboxamide can be produced in a shorter process using inexpensive raw materials, and resulted in the completion of the present invention. Accordingly, the present invention provides the following.

<1> A method of selectively producing an optically active compound represented by the formula [2]

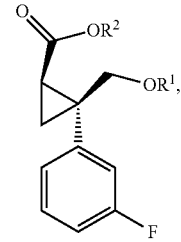

[2]

wherein $R^1$ is an alkylcarbonyl group, and $R^2$ is an alkyl group (hereinafter, the optically active compound represented by the formula [2] is referred to as compound [2]), which comprises Step 1: a step of reacting a compound represented by the formula [1]

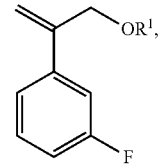

[1]

wherein $R^1$ is as defined above (hereinafter to be referred to as compound [1]), with an alkyl diazoacetate in the presence of copper trifluoromethanesulfonate and an optically active compound represented by the formula [5] or formula [6]

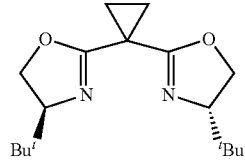

[5]

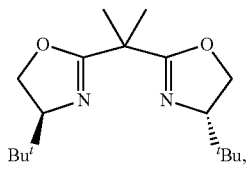

[6]

wherein $^t$Bu is a tert-butyl group (hereinafter, the optically active compound represented by the formula [5] or formula [6] is referred to as compound [5] or compound [6]), in an organic solvent.

<2> A method of producing an optically active compound represented by the formula [4]

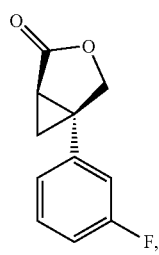

[4]

(hereinafter, the optically active compound represented by the formula [4] is referred to as compound [4]), which comprises Step 1: a step of reacting compound [1] with an alkyl diazoacetate in the presence of copper trifluoromethanesulfonate and compound [5] or compound [6], in an organic solvent to give compound [2], Step 2: a step of subjecting compound [2] obtained in Step 1 to alkaline hydrolysis to give an optically active compound represented by the formula [3]

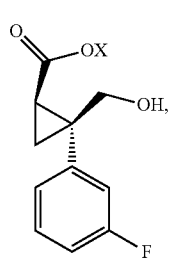

[3]

wherein X is an alkali metal (hereinafter, the optically active compound represented by the formula [3] is referred to as compound [3]), and Step 3: a step of subjecting compound [3] obtained in Step 2 to a cyclization reaction to give compound [4].

<3> A method of producing compound [4], which comprises

Step 1: a step of reacting compound [1] with an alkyl diazoacetate in the presence of copper trifluoromethanesulfonate and compound [5] or compound [6], in an organic solvent to give a mixture comprising compound [2] and an optically active compound represented by the formula [2a]

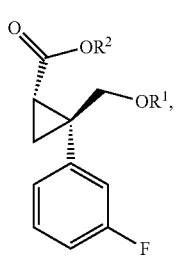

[2a]

wherein $R^1$ and $R^2$ are as defined above (hereinafter, the optically active compound represented by the formula [2a] is referred to as compound [2a]), Step 2: a step of subjecting the mixture obtained in Step 1 to alkaline hydrolysis to give a mixture comprising compound [3] and an optically active compound represented by the formula [3a]

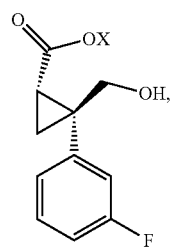

[3a]

wherein X is as defined above (hereinafter, the optically active compound represented by the formula [3a] is referred to as compound [3a]), Step 3a: a step of subjecting compound [3] to cyclization by adjusting the mixture obtained in Step 2 to pH 7.0 or below with an acid to give a mixture comprising compound [4] and an optically active compound represented by the formula [3b]

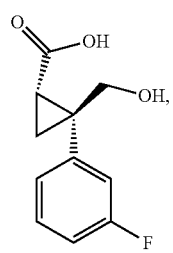

[3b]

(hereinafter, the optically active compound represented by the formula [3b] is referred to as compound [3b]), and Step 3b: a step of subjecting the mixture obtained in Step 3a to an extraction operation with an aromatic hydrocarbon solvent and a liquid separation operation to remove compound [3b] from the mixture.

<4> The method according to any of the above-mentioned [1] to [3], wherein Step 1 is carried out in the presence of copper trifluoromethanesulfonate and compound [5].

<5> The method according to the above-mentioned [3], which further comprises a step of washing the mixture obtained in Step 2 with an aromatic hydrocarbon solvent, and then removing the organic layer.

<6> The method according to any of the above-mentioned [3] to [5], wherein the mixture obtained in Step 3a is adjusted to pH 6.0 to 8.0, before the extraction operation with an aromatic hydrocarbon solvent and the liquid separation operation.

<7> Compound [2].

<8> Compound [3].

<9> Compound [4].

<10> A method of producing an optically active compound represented by the formula [8]

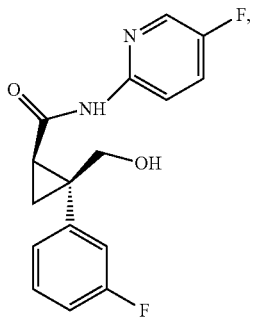
[8]

(hereinafter, the optically active compound represented by the formula [8] is referred to as compound [8]), which comprises Step 4: a step of reacting compound [4] with a compound represented by the formula [7]

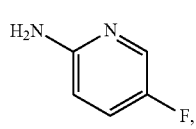
[7]

(hereinafter to be referred to as compound [7]), in the presence of an organic aluminium compound or a base, in an organic solvent.

<11> A method of producing an optically active compound represented by the formula [A]

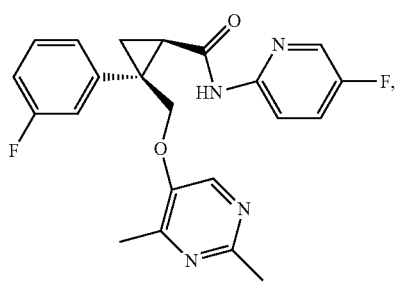
[A]

(hereinafter, the optically active compound represented by the formula [A] is referred to as compound [A]), which comprises Step 4: a step of reacting compound [4] with compound [7] in the presence of an organic aluminium compound or a base, in an organic solvent to give compound [8], and Step 5: a step of subjecting compound [8] obtained in Step 4 to the Mitsunobu reaction with a compound represented by the formula [9]

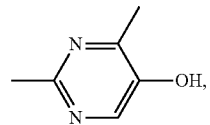
[9]

(hereinafter to be referred to as compound [9])

to give compound [A].

<12> A method of producing compound [A], which comprises

Step 1: a step of reacting compound [1] with an alkyl diazoacetate in the presence of copper trifluoromethanesulfonate and compound [5] or compound [6], in an organic solvent to give compound [2], Step 2: a step of subjecting compound [2] obtained in Step 1 to alkaline hydrolysis to give compound [3], Step 3: a step of subjecting compound [3] obtained in Step 2 to a cyclization reaction to give compound [4], Step 4: a step of reacting compound [4] obtained in Step 3 with compound [7] in the presence of an organic aluminium compound or a base, in an organic solvent to give compound [8], and Step 5: a step of subjecting compound [8] obtained in Step 4 to the Mitsunobu reaction with compound [9] to give compound [A].

[13] Compound [8].

<14> A method of producing compound [A], which comprises

Step 6: a step of subjecting compound [4] to bromination to give an optically active compound represented by the formula

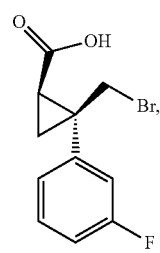
[10]

(hereinafter, the optically active compound represented by the formula [10] is referred to as compound [10]), Step 7: a step of subjecting compound [10] obtained in Step 6 to alkyl esterification to give an optically active compound represented by the formula [11]

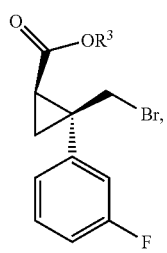
[11]

wherein R³ is an alkyl group (hereinafter, the optically active compound represented by the formula [11] is referred to as compound [11]), Step 8: a step of subjecting compound [11] obtained in Step 7 to tosylation to give an optically active compound represented by the formula [12]

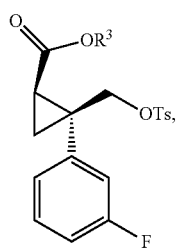

wherein Ts is a tosyl group, and R³ is as defined above (hereinafter, the optically active compound represented by the formula [12] is referred to as compound [12]), Step 9: a step of reacting compound [12] obtained in Step 8 with compound [9] in the presence of a base, in an organic solvent, and then subjecting the resulting compound to alkaline hydrolysis to give an optically active compound represented by the formula [13]

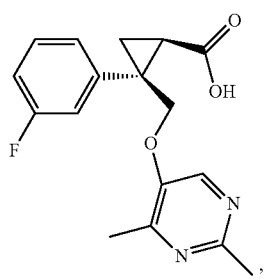

(hereinafter, the optically active compound represented by the formula [13] is referred to as compound [13]), and Step 10: a step of reacting compound [13] obtained in Step 9 with compound [7] in the presence of a base, in an organic solvent to give compound [A].

<15> A method of producing compound [A], which comprises

Step 1: a step of reacting compound [1] with an alkyl diazoacetate in the presence of copper trifluoromethanesulfonate and compound [5] or compound [6], in an organic solvent to give compound [2], Step 2: a step of subjecting compound [2] obtained in Step 1 to alkaline hydrolysis to give compound [3], Step 3: a step of subjecting compound [3] obtained in Step 2 to a cyclization reaction to give compound [4], Step 6: a step of subjecting compound [4] obtained in Step 3 to bromination to give compound [10], Step 7: a step of subjecting compound [10] obtained in Step 6 to alkyl esterification to give compound [11], Step 8: a step of subjecting compound [11] obtained in Step 7 to tosylation to give compound [12], Step 9: a step of reacting compound [12] obtained in Step 8 with compound [9] in the presence of a base, in an organic solvent, and then subjecting the resulting compound to alkaline hydrolysis to give compound [13], and Step 10: a step of reacting compound [13] obtained in Step 9 with compound [7] in the presence of a base, in an organic solvent to give compound [A].

<16> Compound [10].

<17> Compound [11].

<18> Compound [12].

Effect of the Invention

According to the present invention, the objective (1R,2S)-2-{[((2,4-dimethylpyrimidin-5-yl)oxy}methyl]-2-(3-fluorophenyl)-N-(5-fluoropyridin-2-yl)cyclopropane-1-carboxamide (compound [A]) can be produced by an industrially advantageous method, i.e., using inexpensive compound [1] as a raw material, in a shorter process via a novel compound.

DESCRIPTION OF EMBODIMENTS

The present invention is explained in detail below.

Compound [4] can be produced according to the following Step 1 to Step 3.

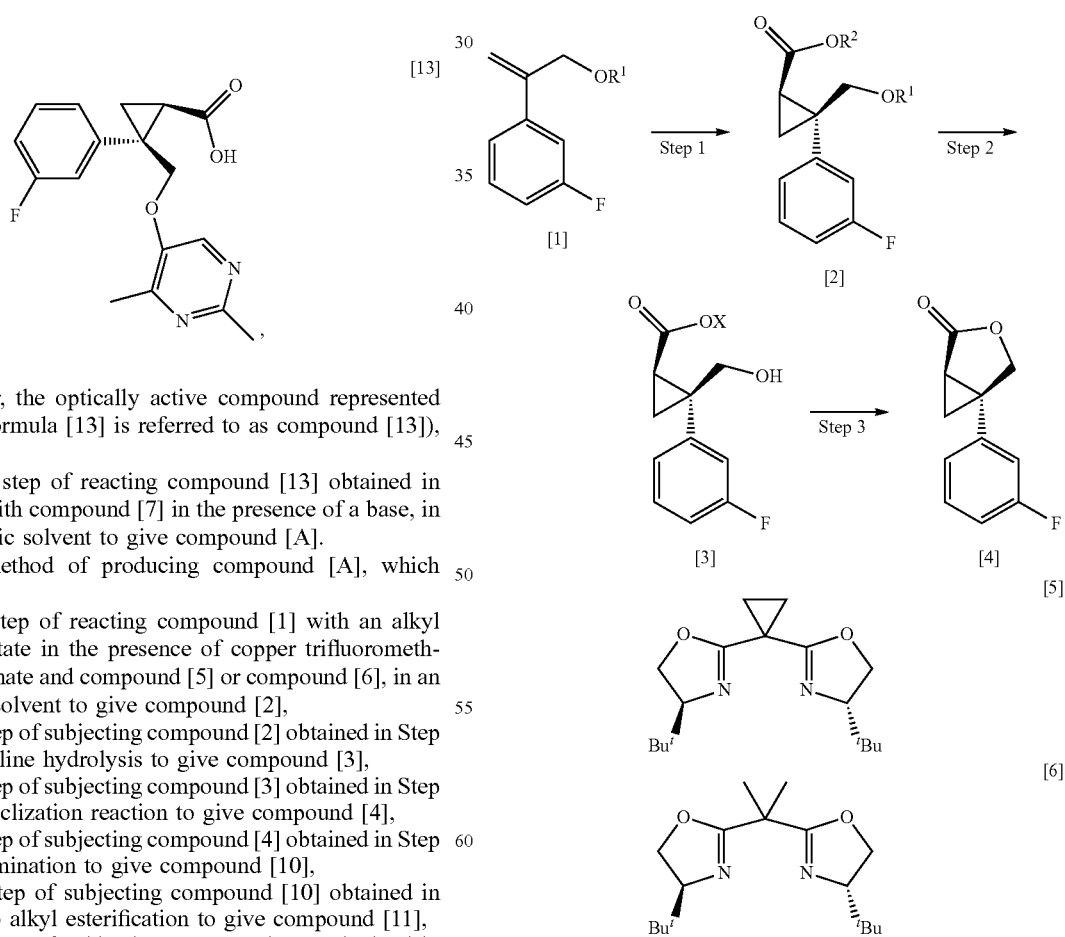

wherein R¹ is an alkylcarbonyl group, R² is an alkyl group, X is an alkali metal, and ⁱBu is a tert-butyl group.

Examples of the "alkylcarbonyl group" represented by $R^1$ include acetyl, propanoyl and the like.

Examples of the "alkyl group" represented by $R^2$ include methyl, ethyl and the like.

Examples of the "alkali metal" represented by X include sodium, potassium, lithium and the like.

Step 1

In this step, compound [1] is reacted with an alkyl diazoacetate in the presence of copper trifluoromethanesulfonate and compound [5] or compound [6], in an organic solvent to selectively give compound [2].

Compound [1] can be produced according to a known method, and compound [1] wherein R is an acetyl is commercially available.

As the alkyl diazoacetate, ethyl diazoacetate is commercially available. Examples of the alkyl group include C1-4 alkyl group, and preferred is a C1-2 alkyl group such as methyl group and ethyl group. The alkyl diazoacetate is prepared from the corresponding glycine alkyl ester by a known diazotization reaction. The amount of the alkyl diazoacetate to be used is generally 0.5 to 2 mol, industrially preferably 0.8 to 1.5 mol, per 1 mol of compound [1], in terms of yield and economy.

The copper trifluoromethanesulfonate and compound [5] or compound [6] form a complex in the reaction system, and the complex acts as an asymmetric catalyst in the reaction of compound [1] with an alkyl diazoacetate (formation of 2S-cyclopropane ring).

The copper trifluoromethanesulfonate is commercially available. For example, it is commercially available as copper (I) trifluoromethanesulfonate ½ toluene complex. The amount of the copper trifluoromethanesulfonate to be used is generally 0.00001 to 0.5 mol, industrially preferably 0.0001 to 0.05 mol, per 1 mol of compound [1], in terms of reactivity, yield (chemical yield, optical yield) and economy.

Compound [5] (1,1-bis [2-((4S)-(1,1-dimethylethyl)-1,3-oxazolinyl)]cyclopropane) and compound [6] (2,2-bis [2-((4S)-(1,1-dimethylethyl)-1,3-oxazolinyl)]propane) can be produced according to a known method, for example, the method described in Journal of Organic Chemistry, 2000, 65, 5875-5878. The amount of compound [5] or compound [6] to be used is generally 0.8 to 5 mol, industrially preferably 0.9 to 2 mol, per 1 mol of copper trifluoromethanesulfonate, in terms of reactivity, yield (chemical yield, optical yield) and economy.

The reaction is preferably carried out in the presence of copper trifluoromethanesulfonate and compound [5], in terms of optical yield.

Examples of the organic solvent include ester solvents (e.g., ethyl acetate, butyl acetate); aromatic hydrocarbon solvents (e.g., toluene, benzene, xylene); halogenated hydrocarbon solvents (e.g., chloroform, dichloromethane, carbon tetrachloride); ether solvents (e.g., diethyl ether, tetrahydrofuran, 1,4-dioxane); aprotic polar solvents (e.g., dimethylformamide, dimethylacetamide); mixed solvents thereof, and the like. The amount of the organic solvent to be used is generally 2 to 30 parts by weight, industrially preferably 4 to 20 parts by weight, per 1 parts by weight of compound [1], in terms of yield and economy.

The reaction is carried out by a method of adding (preferably adding dropwise) a mixture of an alkyl diazoacetate and an organic solvent to a mixture of compound [1], copper trifluoromethanesulfonate, compound [5] or compound [6] and an organic solvent, and the like.

The reaction is carried out generally within the range of −50 to 100° C., preferably within the range of −20 to 80° C., although it depends on the kind of the organic solvent and the like. The reaction time is generally 10 min to 72 hr, preferably 2 hr to 24 hr, although it depends on the kind of the organic solvent, the reaction temperature and the like.

The progress of the reaction can be confirmed by analysis means such as thin layer chromatography, gas chromatography, high-performance liquid chromatography and the like. After completion of the reaction, conventional post-treatments such as liquid separation operation, solvent evaporation and the like are carried out. Although the unreacted compound [1] used as a raw material may remain in the obtained mixture, and the mixture may be directly subjected to Step 2, or compound [2] after isolation and purification may be subjected to Step 2.

By using compound [5] or compound [6], the asymmetric reaction proceeds to form a 2S-cyclopropane ring. As shown below, the mixture obtained in this step contains the trans-form compound [2a] in addition to the cis-form compound [2]. Preferably, compound [2] is not isolated in this step, and the mixture is directly subjected to Step 2.

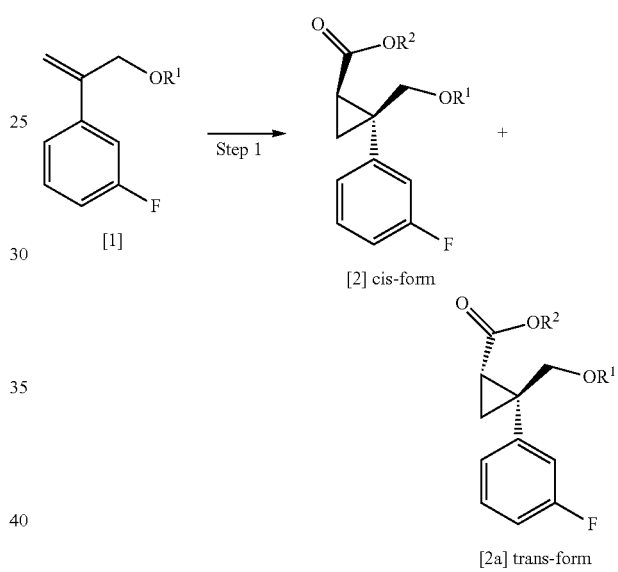

wherein each symbol is as defined above.

Step 2

In this step, compound [2] obtained in Step 1 is subjected to alkaline hydrolysis to give compound [3]. Preferably, the mixture containing compound [2] and compound [2a] obtained in Step 1 without isolation of compound [2] is subjected to alkaline hydrolysis.

Examples of the alkali to be used in the alkaline hydrolysis include sodium hydroxide, potassium hydroxide and the like, and sodium hydroxide is industrially preferably used. The alkali is generally used as an aqueous solution, preferably used as a 5 to 40% aqueous solution.

The alkaline hydrolysis is carried out by mixing compound [2] (preferably the mixture containing compound [2] and compound [2a]) with an alkali aqueous solution.

The reaction is carried out generally within the range of 0 to 100° C., preferably within the range of 20 to 80° C. The reaction time is generally 10 min to 48 hr, preferably 1 hr to 12 hr, although it depends on the reaction temperature and the like.

The progress of the reaction can be confirmed by analysis means such as thin layer chromatography, gas chromatography, high-performance liquid chromatography and the like.

The unreacted compound [1] remaining in the mixture obtained in Step 1 is also present in the mixture after completion of the reaction in this step, and it is preferably removed in this stage. The removal is carried out by washing the mixture containing compound [3] after completion of the reaction with an aromatic hydrocarbon solvent.

Examples of the aromatic hydrocarbon solvent to be used in the washing include toluene, benzene and xylene, and toluene is industrially preferable.

The mixture obtained in this step is an aqueous solution containing compound [3]. Since Step 3 can be carried out in an aqueous system, the mixture can be directly subjected to Step 3.

Compound [2] is converted into compound [3] by hydrolysis. As shown below, compound [2a] contained in the mixture obtained in Step 1 is also converted into compound [3a] by hydrolysis, and therefore, the mixture obtained in this step contains compound [3a] in addition to compound [3]. Preferably, compound [3] is not isolated in this step, and the mixture is directly subjected to Step 3.

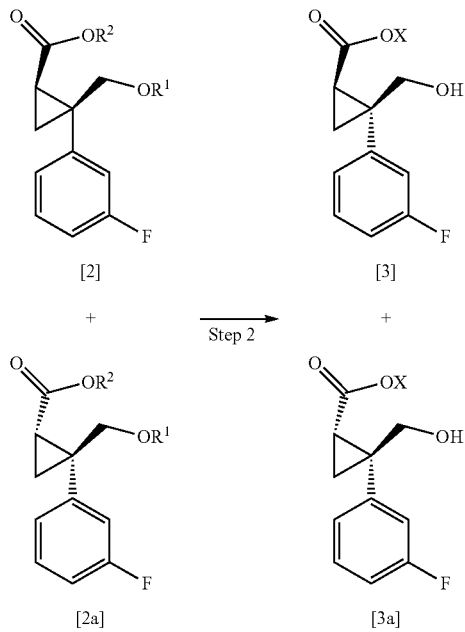

wherein each symbol is as defined above.

Step 3

In this step, compound [3] obtained in Step 2 is subjected to a cyclization reaction to give compound [4]. The mixture containing compound [3] and compound [3a] obtained in Step 2 without isolation of compound [3] is preferably subjected to a cyclization reaction (Step 3a).

The cyclization reaction is carried out by adjusting the reaction system to pH 7.0 or below, preferably pH 5 or below, with an acid.

Examples of the acid to be used in the acid treatment include hydrogen chloride, sulfuric acid, nitric acid and the like, and hydrogen chloride is industrially preferable. The hydrogen chloride used is generally hydrochloric acid, preferably 5 to 35% hydrochloric acid.

The cyclization reaction is carried out by addition (preferably dropwise addition) of an acid to the reaction system containing compound [3] (preferably the mixture containing compound [3] and compound [3a]).

The reaction is carried out generally within the range of 0 to 100° C., preferably within the range of 20 to 80° C. The reaction time is generally 10 min to 48 hr, preferably 2 hr to 12 hr, although it depends on the reaction temperature and the like.

The progress of the reaction can be confirmed by analysis means such as thin layer chromatography, gas chromatography, high-performance liquid chromatography and the like.

Compound [3a] contained in the mixture obtained in Step 2 is only converted into compound [3b] in this step, and does not undergo the cyclization reaction. Compound [3b] can be removed by an extraction operation and a liquid separation operation (Step 3b).

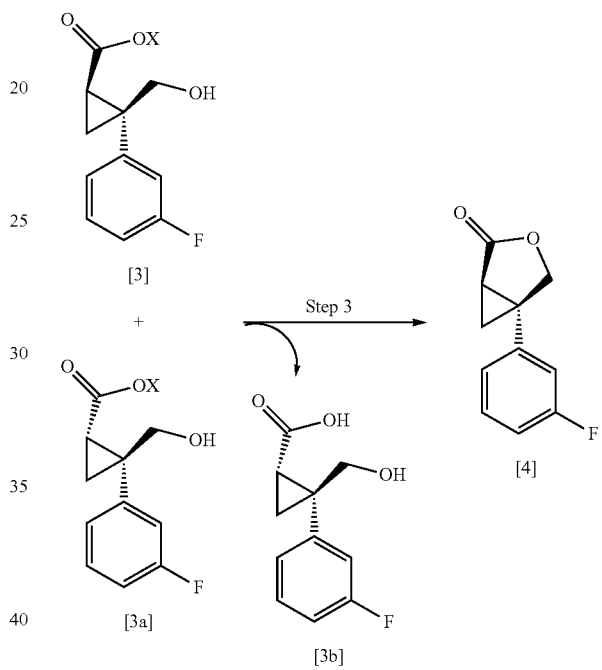

wherein each symbol is as defined above.

Specifically, the mixture after completion of the reaction is adjusted to preferably pH 5 to 8, more preferably pH 6.0 to 8.0, and then extracted with an organic solvent to transfer compound [4] to the organic layer. Then, compound [3b] is converted into compound [3a] and transferred to the aqueous layer.

Examples of the organic solvent to be used in the extraction include aromatic hydrocarbon solvents (e.g., toluene, benzene, xylene); ester solvents (e.g., ethyl acetate, butyl acetate); halogenated hydrocarbon solvents (e.g., chloroform, dichloromethane, carbon tetrachloride); ether solvents (e.g., diethyl ether) and the like, and preferred are aromatic hydrocarbon solvents, and particularly preferred is toluene, in terms of extraction efficiency.

After extraction, the organic layer and the aqueous layer are separated by a liquid separation operation. Where necessary, the extraction operation of the aqueous layer and the liquid separation operation may be repeated.

Compound [4] can be isolated by concentrating the obtained organic layer. Where necessary, compound [4] may be purified by methods such as silica gel column chromatography, distillation and the like.

Compound [4] thus obtained can be converted into the objective compound [A] ((1R,2S)-2-{[((2,4-dimethylpyrimidin-5-yl)oxy}methyl]-2-(3-fluorophenyl)-N-(5-fluoropyridin-2-yl)cyclopropane-1-carboxamide) by the following steps.

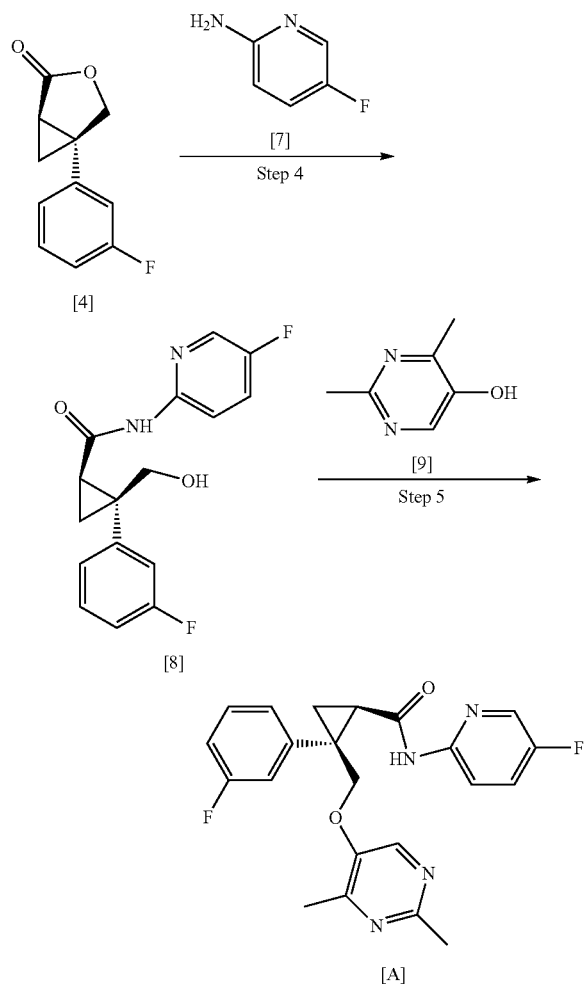

Step 4

In this step, compound [4] is reacted with compound [7] in the presence of an organic aluminium compound or a base, in an organic solvent to give compound [8].

Compound [7] is commercially available product. The amount of compound [7] to be used is generally 0.8 to 5 mol, industrially preferably 0.9 to 2 mol, per 1 mol of compound [4], in terms of yield and economy.

Example of the organic aluminium compound include diisobutylaluminium hydride, trimethylaluminium and the like. Examples of the base include alkali metal alcoholates such as sodium methoxide and the like, and butyllithium.

The amount of the organic aluminium compound or base to be used is generally 0.8 to 5 mol, industrially preferably 0.9 to 2 mol, per 1 mol of compound [4], in terms of yield and economy.

Examples of the organic solvent include ether solvents (e.g., diethyl ether, tetrahydrofuran, 1,4-dioxane); aromatic hydrocarbon solvents (e.g., toluene, benzene, xylene); halogenated hydrocarbon solvents (e.g., chloroform, dichloromethane, carbon tetrachloride); mixed solvents thereof, and the like. The amount of the organic solvent to be used is generally 2 to 100 parts by weight, industrially preferably 5 to 20 parts by weight, per 1 parts by weight of compound [4], in terms of yield and economy.

The reaction is carried out by a method of adding (preferably adding dropwise) a mixture of compound [4] and an organic solvent to a mixture of compound [7], a base and an organic solvent, and the like.

The reaction is carried out generally within the range of −80 to 100° C., preferably within the range of −40 to 80° C., although it depends on the kind of the organic solvent and the like. The reaction time is generally 10 min to 48 hr, preferably 1 hr to 24 hr, although it depends on the kind of the organic solvent, the reaction temperature and the like.

The progress of the reaction can be confirmed by analysis means such as thin layer chromatography, gas chromatography, high-performance liquid chromatography and the like. After completion of the reaction, compound [8] can be isolated by conventional post-treatments such as solvent extraction, liquid separation operation, solvent evaporation and the like. Where necessary, compound [8] may be purified by methods such as silica gel column chromatography, recrystallization and the like.

Step 5

In this step, compound [8] is subjected to the Mitsunobu reaction with compound [9] to give compound [A]. The Mitsunobu reaction is carried out by reacting compound [8] with compound [9] in the presence of an azodicarboxylic acid diester and triphenylphosphine in an organic solvent.

Examples of the azodicarboxylic acid diester include ditert-butyl azodicarboxylate, diethyl azodicarboxylate and the like. The amount of the azodicarboxylic acid diester to be used is generally 0.8 to 5 mol, industrially preferably 0.9 to 2 mol, per 1 mol of compound [8], in terms of yield and economy.

The amount of the triphenylphosphine to be used is generally 0.2 to 5 mol, industrially preferably 0.5 to 2 mol, per 1 mol of azodicarboxylic acid diester, in terms of yield and economy.

The amount of compound [9] to be used is generally 0.8 to 5 mol, industrially preferably 0.9 to 2 mol, per 1 mol of compound [8], in terms of yield and economy.

Examples of the organic solvent include ether solvents (e.g., diethyl ether, tetrahydrofuran, 1,4-dioxane); ester solvents (e.g., ethyl acetate, butyl acetate); aromatic hydrocarbon solvents (e.g., toluene, benzene, xylene); halogenated hydrocarbon solvents (e.g., chloroform, dichloromethane, carbon tetrachloride); mixed solvents thereof, and the like. The amount of the organic solvent to be used is generally 2 to 100 parts by weight, industrially preferably 4 to 30 parts by weight, per 1 parts by weight of compound [8], in terms of yield and economy.

The reaction is carried out by a method of adding (preferably adding dropwise) triphenylphosphine and a mixture of an azodicarboxylic acid diester and an organic solvent to a mixture of compound [8], compound [9] and an organic solvent, and the like.

The reaction is carried out generally within the range of −50 to 100° C., preferably within the range of −20 to 80° C., although it depends on the kind of the organic solvent and the like. The reaction time is generally 10 min to 48 hr, preferably 1 hr to 24 hr, although it depends on the kind of the organic solvent, the reaction temperature and the like.

The progress of the reaction can be confirmed by analysis means such as thin layer chromatography, high-performance liquid chromatography and the like. After completion of the reaction, compound [A] can be isolated by conventional post-treatments such as solvent extraction, liquid separation operation, solvent evaporation and the like. Where necessary, compound [A] may be purified by methods such as silica gel column chromatography, recrystallization and the like.

Alternatively, compound [4] can also be converted into the objective compound [A] (1R,2S)-2-{[((2,4-dimethylpyrimidin-5-yl)oxy}methyl]-2-(3-fluorophenyl)-N-(5-fluoropyridin-2-yl)cyclopropane-1-carboxamide by the following steps.

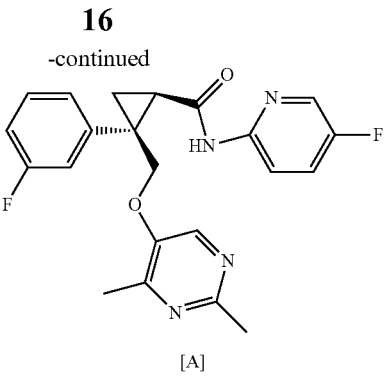

[A]

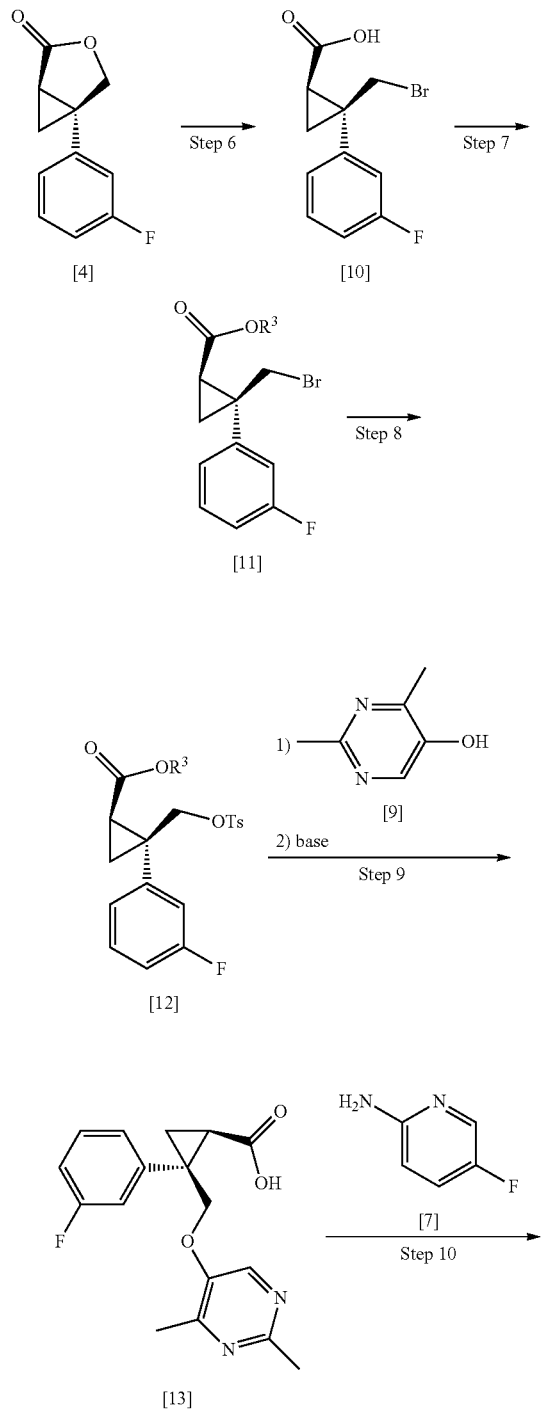

wherein Ts is a tosyl group, and $R^3$ is an alkyl group.

Examples of the "alkyl group" represented by $R^3$ include methyl, ethyl and the like.

Step 6

In this step, compound [4] is subjected to bromination to give compound [10].

The bromination is carried out by reacting compound [4] with a brominating agent in an organic solvent.

Examples of the brominating agent include hydrogen bromide/acetic acid solution and the like. The amount of the brominating agent to be used is generally 1 to 100 mol, industrially preferably 2 to 50 mol, per 1 mol of compound [4], in terms of yield and economy.

Examples of the organic solvent include organic acids (e.g., acetic acid); ether solvents (e.g., diethyl ether, tetrahydrofuran, 1,4-dioxane); aromatic hydrocarbon solvents (e.g., toluene, benzene, xylene); halogenated hydrocarbon solvents (e.g., chloroform, dichloromethane, carbon tetrachloride); mixed solvents thereof, and the like. When hydrogen bromide/acetic acid solution is used as a brominating agent, then acetic acid also serves as a solvent.

The reaction is carried out by a method of mixing compound [4], a brominating agent and an organic solvent, and the like.

The reaction is carried out generally within the range of −20 to 150° C., preferably within the range of 0 to 100° C., although it depends on the kind of the organic solvent and the like. The reaction time is generally 30 min to 72 hr, preferably 4 hr to 48 hr, although it depends on the kind of the organic solvent, the reaction temperature and the like.

The progress of the reaction can be confirmed by analysis means such as thin layer chromatography, high-performance liquid chromatography and the like. After completion of the reaction, compound [10] can be isolated by conventional post-treatments such as solvent extraction, liquid separation operation, solvent evaporation and the like. Where necessary, compound [10] may be purified by methods such as silica gel column chromatography, recrystallization and the like.

Step 7

In this step, compound [10] is subjected to alkyl esterification to give compound [11].

The alkyl esterification is carried out by reacting compound [10] with an alkyl alcohol such as ethanol, methanol and the like, in the presence of an acid catalyst.

Examples of the acid catalyst include p-toluenesulfonic acid, sulfuric acid, methanesulfonic acid and the like. Although the amount of the acid catalyst to be used is a catalytic amount, it is generally 0.001 to 1 mol, industrially preferably 0.005 to 0.5 mol, per 1 mol of compound [10], in terms of yield and economy. Although the amount of the ethanol to be used is a solvent amount, it is generally 2 to 500 mol, industrially preferably 10 to 200 mol, per 1 mol of compound [10], in terms of yield and economy.

The reaction is carried out by a method of mixing compound [10], an alkyl alcohol and an acid catalyst, and the like.

The reaction is carried out generally within the range of 0 to 100° C., preferably within the range of 25 to 90° C. The reaction time is generally 30 min to 72 hr, preferably 2 hr to 48 hr, although it depends on the kind of the organic solvent, the reaction temperature and the like.

The progress of the reaction can be confirmed by analysis means such as thin layer chromatography, high-performance liquid chromatography and the like. After completion of the reaction, compound [11] can be isolated by conventional post-treatments such as solvent extraction, liquid separation operation, solvent evaporation and the like. Where necessary, compound [11] may be purified by methods such as silica gel column chromatography, recrystallization and the like.

Step 8

In this step, compound [11] is subjecting to tosylation to give compound [12].

The tosylation is carried out by reacting compound [11] with a tosylating agent in an organic solvent.

Examples of the tosylating agent include silver p-toluenesulfonate. The amount of the tosylating agent to be used is generally 0.8 to 5 mol, industrially preferably 0.9 to 2 mol, per 1 mol of compound [11], in terms of yield and economy.

Examples of the organic solvent include nitrile solvents (e.g., acetonitrile); ether solvents (e.g., diethyl ether, tetrahydrofuran, 1,4-dioxane); ester solvents (e.g., ethyl acetate, butyl acetate); aromatic hydrocarbon solvents (e.g., toluene, benzene, xylene); halogenated hydrocarbon solvents (e.g., chloroform, dichloromethane, carbon tetrachloride); mixed solvents thereof, and the like. Among them, acetonitrile is preferably used in terms of reactivity and yield. The amount of the organic solvent to be used is generally 2 to 100 parts by weight, industrially preferably 4 to 20 parts by weight, per 1 parts by weight of compound [11], in terms of yield and economy.

The reaction is carried out by a method of mixing compound [11], a tosylating agent and an organic solvent, and the like.

The reaction is carried out generally within the range of −20 to 100° C., preferably within the range of 20 to 80° C. The reaction time is generally 10 min to 48 hr, preferably 1 hr to 24 hr, although it depends on the kind of the organic solvent, the reaction temperature and the like.

The progress of the reaction can be confirmed by analysis means such as thin layer chromatography, high-performance liquid chromatography and the like. After completion of the reaction, compound [12] can be isolated by conventional post-treatments such as solvent extraction, liquid separation operation, solvent evaporation and the like. Where necessary, compound [12] may be purified by methods such as silica gel column chromatography, recrysallization and the like.

Step 9

In this step, compound [12] is reacted with compound [9] in the presence of a base, in an organic solvent, followed by alkaline hydrolysis to give compound [13].

Examples of the base include cesium carbonate, potassium carbonate, sodium carbonate and the like. The amount of the base to be used is generally 0.01 to 10 mol, industrially preferably 0.5 to 5 mol, per 1 mol of compound [12], in terms of yield and economy.

The amount of compound [9] to be used is generally 0.8 to 5 mol, industrially preferably 0.9 to 2 mol, per 1 mol of compound [12], in terms of yield and economy.

Examples of the organic solvent include nitrile solvents (e.g., acetonitrile); ether solvents (e.g., diethyl ether, tetrahydrofuran, 1,4-dioxane); ester solvents (e.g., ethyl acetate, butyl acetate); aromatic hydrocarbon solvents (e.g., toluene, benzene, xylene); halogenated hydrocarbon solvents (e.g., chloroform, dichloromethane, carbon tetrachloride); mixed solvents thereof, and the like. Among the, acetonitrile is preferably used in terms of reactivity and yield. The amount of the organic solvent to be used is generally 2 to 100 parts by weight, industrially preferably 4 to 20 parts by weight, per 1 parts by weight of compound [12], in terms of yield and economy.

The reaction is carried out by a method of adding a base to a mixture of compound [12], compound [9] and an organic solvent, and the like.

The reaction is carried out generally within the range of −20 to 100° C., preferably within the range of 20 to 80° C. The reaction time is generally 10 min to 48 hr, preferably 1 hr to 24 hr, although it depends on the kind of the organic solvent, the reaction temperature and the like.

The progress of the reaction can be confirmed by analysis means such as thin layer chromatography, high-performance liquid chromatography and the like. After completion of the reaction, conventional post-treatments such as solvent extraction, liquid separation operation, solvent evaporation and the like are carried out.

Subsequently, alkaline hydrolysis is carried out.

Examples of the alkali to be used in the alkaline hydrolysis include sodium hydroxide, potassium hydroxide and the like, and sodium hydroxide is industrially preferably used. The alkali is generally used as an aqueous solution, preferably 1 to 40% aqueous solution.

The alkaline hydrolysis is carried out by mixing the mixture after the post-treatment with an alkali aqueous solution.

The reaction is carried out generally within the range of 0 to 100° C., preferably within the range of 10 to 80° C. The reaction time is generally 30 min to 72 hr, preferably 1 hr to 24 hr, although it depends on the reaction temperature and the like.

The progress of the reaction can be confirmed by analysis means such as thin layer chromatography, gas chromatography, high-performance liquid chromatography and the like. After completion of the reaction, compound [13] can be isolated by conventional post-treatments such as solvent extraction, liquid separation operation, solvent evaporation and the like. Where necessary, compound [13] may be purified by methods such as silica gel column chromatography, recrystallization and the like.

Step 10

In this step, compound [13] is reacted with compound [7] in the presence of a base, in an organic solvent to give the objective compound [A]. The step can be carried out according to the method described in Patent Document 1.

EXAMPLES

Hereinafter, the present invention is explained in more detail with reference to Examples, but the present invention is not limited thereto. The conditions of the HPLC analysis performed in the following examples are shown below.

HPLC Analysis Condition 1 (Chemical Purity)
  column: Waters SunFire C18 (3×150 mm, 3.5 μm)
  temperature: 40° C.

flow rate: 0.5 ml/min mobile phase A: water/trifluoroacetic acid=1000/1 mobile phase B: acetonitrile/trifluoroacetic acid=1000/1 gradient:

TABLE 1

| Time (min) | mobile phase A(%) | mobile phase B(%) |
|---|---|---|
| 0 | 95 | 5 |
| 3 | 30 | 70 |
| 30 | 30 | 70 |
| 40 | 10 | 90 |
| 50 | 10 | 90 |
| 50.1 | 95 | 5 |
| 60 | 95 | 5 | detector: UV 210 nm

HPLC Analysis Condition 2 (Optical Purity)

column: CHIRALPAK IB (4.6×150 mm, 5 μm)

temperature: 25° C.

flow rate: 1.0 ml/min mobile phase: water/methanol=40/60 detector: UV 254 nm injection: 10 μl

Example 1-1 Synthesis of Compound [2A]

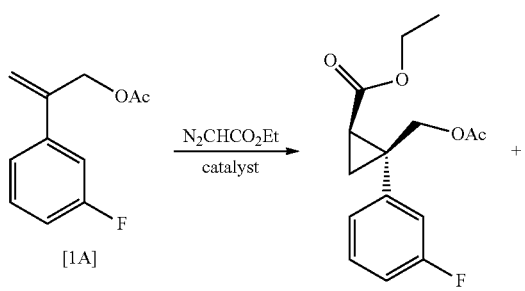

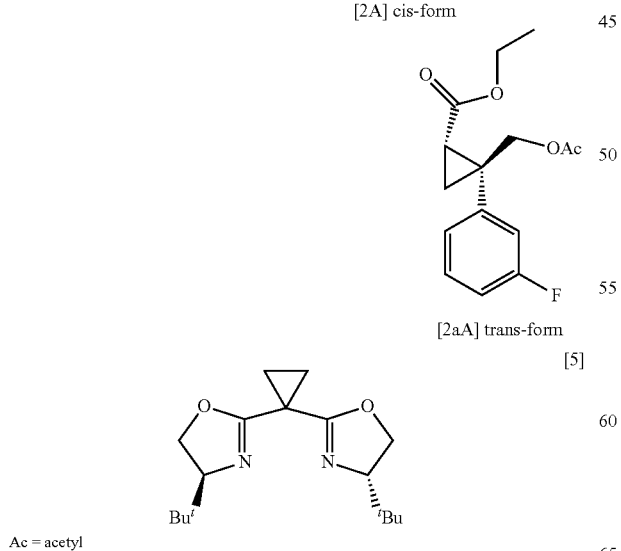

Ac = acetyl

At room temperature, in a 200 ml separable flask, compound [1A] (3.50 g, 18.02 mmol), compound [5] (52.70 mg, 0.18 mmol), copper (I) trifluoromethanesulfonate ½ toluene complex (46.26 mg, 0.18 mmol) and ethyl acetate (35 ml) were charged and mixed. Then, a 15% toluene solution of ethyl diazoacetate (20.56 g, 27.03 mmol) was added dropwise thereto over 4 hr, and the mixture was stirred for 2 hr as it was. After standing, the mixture was concentrated under reduced pressure to give a concentrated residue (6.48 g).

HPLC purity (HPLC analysis condition 1): peak area normalization of 47.3% in LC chromatogram of the cis-form (compound [2A]), 11.70% of the unreacted compound [1A], the cis-form ([2A])/the trans-form ([2aA])=76.7:23.3, optical purity of the cis-form (HPLC analysis condition 2): 98.02% e.e.

Example 1-2 Synthesis of Compound [2A]

At room temperature, in a 200 ml separable flask, compound [1A] (3.00 g, 15.45 mmol), compound [5] (45.20 mg, 0.15 mmol), copper(I) trifluoromethanesulfonate ½ toluene complex (39.90 mg, 0.15 mmol) and ethyl acetate (30 ml) were charged and mixed. Then, a 15% toluene solution of ethyl diazoacetate (14.21 g, 18.68 mmol) was added dropwise thereto over 4 hr, and the mixture was stirred for 1 hr as it was. After standing, the mixture was concentrated under reduced pressure to give a concentrated residue (4.88 g). HPLC purity (HPLC analysis condition 1): peak area normalization of 42.5% in LC chromatogram of the cis-form (compound [2A]), 24.3% of the unreacted compound [1A], the cis-form ([2A])/the trans-form ([2aA])=76.5:23.5, optical purity of the cis-form (HPLC analysis condition 2): 96.54% e.e.

The concentrated residue was purified by silica gel column chromatography to give compound [2A] (0.91 g).

LC-MS(ESI)[M+H]$^+$ 281

HPLC purity (HPLC analysis condition 1): 87.9%, the cis-form ([2A])/the trans-form ([2aA])=97.8:2.2.

$^1$HNMR (400 MHZ, CDCl$_3$) δ7.12-7.08 (m, 1H), 6.97-6.78 (m, 3H), 4.41 (d, J=11.6 Hz, 1H), 4.18 (d, J=11.6 Hz, 1H), 4.09-4.01 (m, 2H), 1.94 (dd, J=5.7, 8.0 Hz, 1H), 1.80 (s, 3H), 1.50-1.48 (m, 1H), 1.30-1.26 (m, 1H), 1.16-1.12 (m, 3H)

Example 2 Synthesis of Compound [2A]

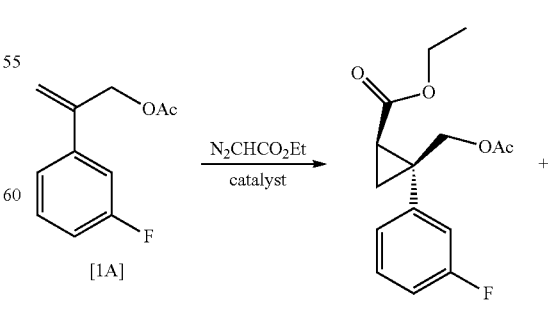

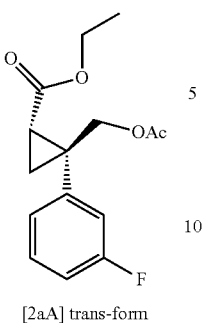

[2aA] trans-form

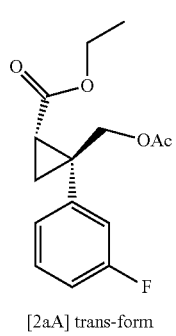

[2aA] trans-form

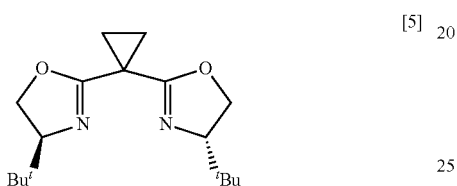

[5]

Ac = acetyl

At room temperature, in a 200 ml separable flask, compound [1A] (7.52 g, 38.72 mmol) and ethyl acetate (65 mL) were charged, and a solution prepared by dissolving compound [5] (113.23 mg, 0.39 mmol) and copper (I) trifluoromethanesulfonate ½ toluene complex (100.17 mg, 0.39 mmol) in ethyl acetate (10 ml) were added thereto, and mixed. Then, the temperature was adjusted to 25° C., a 15% toluene solution of ethyl diazoacetate (44.18 g, 58.08 mmol) was added dropwise thereto over 4 hr, and the mixture was stirred for 1 hr as it was. After standing, the mixture was concentrated under reduced pressure to give a concentrated residue (14.1 g). HPLC purity (HPLC analysis condition 1): peak area normalization of 43.4% in LC chromatogram of the cis-form (compound [2A]), 15.29% of the unreacted compound [1A], the cis-form ([2A])/the trans-form ([2aA]) =76.9:23.1, optical purity of the cis-form (HPLC analysis condition 2): 96.13% e.e.

Example 3 Synthesis of Compound [2A]

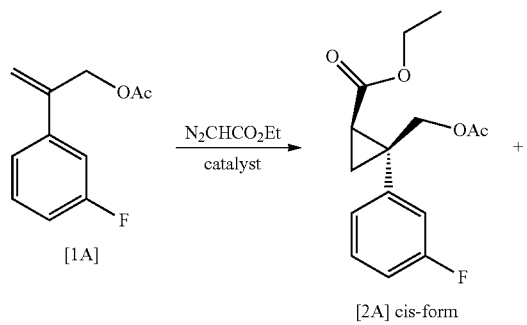

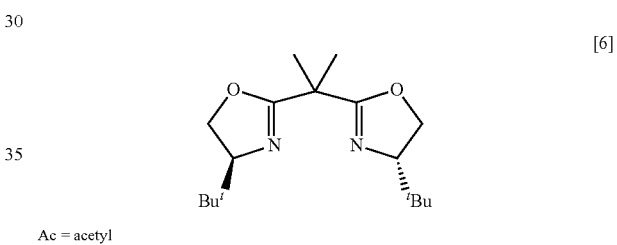

[6]

Ac = acetyl

At room temperature, compound [1A] (350 mg, 1.8 mmol), compound [6] (5.31 mg, 0.018 mmol), copper (I) trifluoromethanesulfonate ½ toluene complex (4.66 mg, 0.018 mmol) and ethyl acetate (3.5 ml) were charged and mixed. Then, a 15% toluene solution of ethyl diazoacetate (2.06 g, 2.7 mmol) was added dropwise thereto over 4 hr, and the mixture was stirred for 1 hr as it was. The mixture was washed with water (3.5 ml). After standing, the mixture was subjected to liquid separation, and the organic layer was separated. The organic layer was concentrated under reduced pressure.

HPLC purity (HPLC analysis condition 1): peak area normalization of 26.0% in LC chromatogram of the cis-form (compound [2A]), 46.10% of the unreacted compound [1A], yield of the cis-form 26.0%, the cis-form ([2A])/the trans-form ([2aA])=73.2:26.8, optical purity of the cis-form (HPLC analysis condition 2): 98.2% e.e.

Example 4 Synthesis of Compound [4]

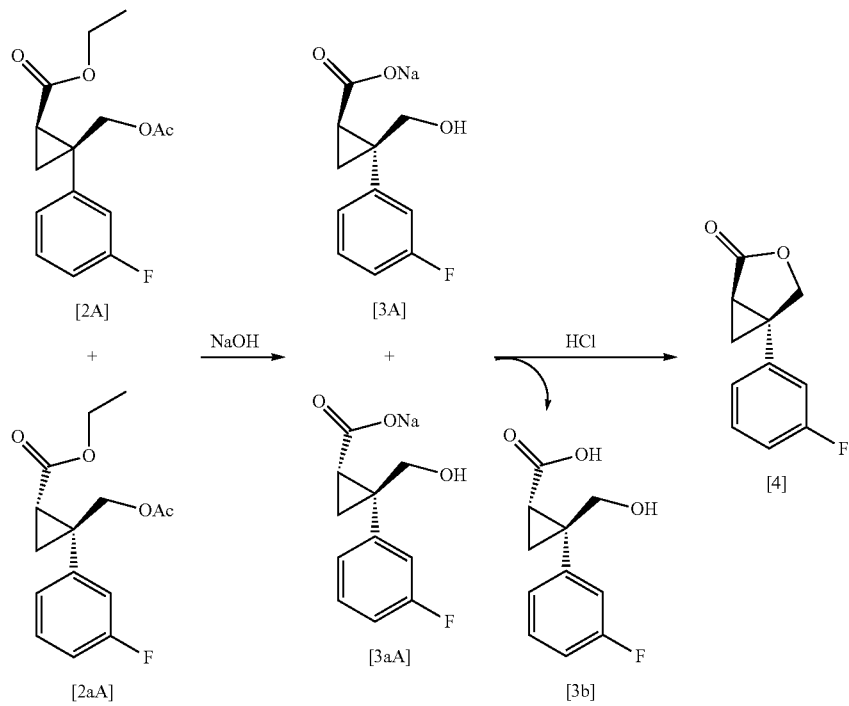

Ac = acetyl

At room temperature, in a 100 ml four neck flask, the mixture of compound [2A] and [2aA] synthesized in Example 2 (7.00 g, pure content of the cis-form 10.88 mmol) and 20% aqueous sodium hydroxide solution (27.47 g, 137.3 mmol) were charged and mixed. Then, the mixture was warmed to 50° C., and stirred for 2 hr. Then, the mixture was cooled to room temperature, toluene (24.25 g) and water (3.50 g) were added thereto, and the mixture was stirred for 30 min as it was. After standing, the mixture was subjected to liquid separation, and the aqueous layer was separated. To the aqueous layer was added 35% hydrochloric acid (15.61 g, 149.8 mmol) over 30 min at room temperature, and the mixture was stirred for 2 hr as it was. Then, 10% aqueous sodium hydroxide solution (20.36 g, 50.9 mmol) was added thereto, and the mixture was stirred at room temperature for 1 hr to adjust the pH to about 6.4. After standing, the mixture was subjected to liquid separation, and the organic layer and the aqueous layer were separated. To the aqueous layer were added toluene (28.01 g) and water (2.00 g), and the mixture was stirred for 30 min as it was. After standing, the mixture was subjected to liquid separation, and the organic layer was separated. This organic layer and the first separated organic layer were combined, and concentrated under reduced pressure to give compound [4] (2.10 g, crude yield 97.3%) (HPLC purity (HPLC analysis condition 1): 96.89%). $^1$HNMR (400 MHz, CDCl$_3$) δ7.29-7.24 (m, 1H), 6.98-6.87 (m, 3H), 4.44-4.36 (m, 2H), 2.28-2.25 (m, 1H), 1.64-1.60 (m, 1H), 1.32 (dd, J=4.8, 3.6H2, 1H)
LC-MS (APCI) [M+H]$^+$ 193

Example 5 Synthesis of Compound [8]

At room temperature, compound [7] (0.29 g, 2.6 mmol) and dehydrated THF (2.0 g) were charged, and the mixture was cooled to −23° C. 17% Diisobutylaluminium hydride/toluene solution (2.50 g, 3.0 mmol) and dehydrated THF (0.5 g) were added dropwise thereto, and the mixture was stirred at −20 to −23° C. for 20 min, and then at 25° C. to 34° C. for 3 hr. The reaction solution was cooled to −5° C., a solution prepared by mixing compound [4] (0.50 g, 2.6 mmol) with dehydrated THF (1.75 g) was added dropwise thereto, and then the mixture was warmed to room temperature, and stirred for 5 hr. Water (2.25 g) and 4N hydrochloric acid (1.95 ml) were ice-cooled, the reaction mixture was added dropwise thereto, and the mixture was warmed to room temperature, and stirred for 30 min. Next, 2-methyltetrahydrofuran (2.5 g) was added thereto, and the mixture was stirred at room temperature for 30 min. After standing, the mixture was subjected to liquid separation, 2-methyltetrahydrofuran (2.5 g) was added to the aqueous layer, and the mixture was stirred for 30 min. After standing, the mixture was subjected to liquid separation, and the obtained organic layer and the first separated organic layer were combined. 1N Hydrochloric acid (2.6 ml) was added thereto, and the mixture was stirred for 30 min. After standing, the mixture was subjected to liquid separation, and to the obtained organic layer was added sodium sulfate (1.00 g), and the mixture was stirred at room temperature for 30 min. The sodium sulfate was removed by filtration, and washed with 2-methyltetrahydrofuran, the filtrate and the washing were concentrated under reduced pressure to give a concentrated residue (0.76 g, crude yield 96%) as a pale-yellow solid.

(HPLC purity (HPLC analysis condition 1): 80.5%).

LC-MS (APCI) [M+H]$^+$ 305

$^1$HNMR (400 MHZ, DMSO-d$_6$) δ11.01 (s, 1H), 8.33 (d, J=2.8 Hz, 1H), 8.19-8.16 (m, 1H), 7.76-7.71 (m, 1H), 7.36-7.27 (m, 2H), 7.05 (d, J=2.8 Hz, 1H), 4.56 (t, J=5.0 Hz, 1H), 3.86 (dd, J=11.2, 4.4 Hz, 1H), 3.75 (dd, J=11.2, 5.2 Hz, 1H), 2.40 (dd, J=8.0, 6.4 Hz, 1H), 1.50-1.48 (m, 1H), 1.29 (dd, J=7.6, 4.4 Hz, 1H)

Example 6 Synthesis of Compound [A]

At room temperature, compound [8] (0.10 g, 0.33 mmol), compound [9] (0.073 g, 0.59 mmol) and dehydrated THF (3 ml) were charged, triphenylphosphine (0.14 g, 0.53 mmol) and 20% di-t-butyl azodicarboxylate/toluene solution (0.49 g, 0.43 mmol) were added thereto, and the mixture was stirred at room temperature for 4 hr. The reaction mixture was added dropwise to water (5.0 g), and the mixture was stirred at room temperature for 30 min. After standing, the mixture was subjected to liquid separation, MTBE (1.0 g) was added to the aqueous layer, and the mixture was stirred for 30 min. The operations were repeated twice. The organic layers were combined, sodium sulfate (1.0 g) was added thereto, and the mixture was stirred at room temperature for 13 hr. The sodium sulfate was removed by filtration, and washed with MTBE, and the filtrate and the washing were concentrated under reduced pressure to give a concentrated residue (0.52 g). The residue was purified by silica gel column chromatography to give a white powder (0.06 g, yield 44%).

(HPLC purity (HPLC analysis condition 1): 99.7%).

LC-MS (APCI) [M+H]$^+$ 411

$^1$HNMR (400 MHZ, DMSO-d$_6$) δ11.22 (s, 1H), 8.33 (d, J=2.8 Hz, 1H), 8.13 (s, 1H), 7.91-7.89 (m, 1H), 7.67-7.62 (m, 1H), 7.46-7.40 (m, 3H), 7.14-7.09 (m, 1H), 4.68 (d, J=10.4 Hz, 1H), 4.29 (d, J=10.4 Hz, 1H), 2.63 (t, J=7.0 Hz, 1H), 2.38 (s, 3H), 2.04 (s, 3H), 1.72-1.69 (m, 1H), 1.52-1.49 (m, 1H)

Example 7 Synthesis of Compound

At room temperature, compound [4] (0.50 g, 2.6 mmol) and 25% hydrogen bromide/acetic acid solution (10.10 g, 31.2 mmol) were charged, and the mixture was warmed to 80° C. The mixture was stirred at 80° C. for 11.5 hr, 25% hydrogen bromide/acetic acid solution (2.40 g, 7.4 mmol) was added thereto, and the mixture was stirred at 80° C. for additional 10 hr. The reaction solution was added dropwise to a solution prepared by mixing water (50.0 g) and toluene (50.0 g), and the mixture was stirred at room temperature for 30 min. After standing, the mixture was subjected to liquid separation, sodium sulfate (5.00 g) and activated carbon (0.50 g) were added to the organic layer, and the mixture was stirred at room temperature for 1 hr. The sodium sulfate and activated carbon were removed by filtration, and washed with toluene (10 g), and the filtrate and the washing were concentrated under reduced pressure to give a concentrated residue (0.75 g, crude yield 106%).

(HPLC purity (HPLC analysis condition 1): 88.6%).

Example 8 Synthesis of Compound [11A]

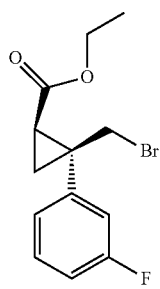

[11A]

At room temperature, compound [10] (0.60 g, 2.2 mmol), p-toluenesulfonic acid monohydrate (0.08 g, 0.42 mmol) and ethanol (12.0 g) were charged, and the mixture was warmed to 80° C., and stirred for 20 hr. The reaction mixture was concentrated under reduced pressure, water (6.0 g) and toluene (6.0 g) were added thereto, and the mixture was stirred at room temperature for 30 min. After standing, the mixture was subjected to liquid separation, water (6.0 g) was added to the organic layer, and the mixture was stirred at room temperature for 30 min. After standing, the mixture was subjected to liquid separation, and the organic layer was concentrated under reduced pressure to give a concentrated residue (0.65 g, crude yield 98%).

(HPLC purity (HPLC analysis condition 1): 80.0%).

Example 9 Synthesis of Compound [12A]

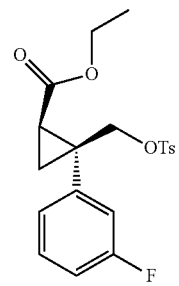

[12A]

At room temperature, compound [11A] (0.56 g, 1.9 mmol), silver p-toluenesulfonate (0.057 g, 2.0 mmol) and acetonitrile (5.6 g) were charged, and the mixture was warmed to 80° C., and stirred for 10 hr. The reaction mixture was cooled to room temperature, 2-methyltetrahydrofuran (11.2 g) and water (11.2 g) were added thereto, and the mixture was stirred at room temperature for 30 min. After standing, the mixture was subjected to liquid separation, 2-methyltetrahydrofuran (5.6 g) was added to the aqueous layer, and the mixture was stirred at room temperature for 30 min. After standing, the mixture was subjected to liquid separation. The obtained organic layer and the first separated organic layer were combined, water (5.6 g) was added thereto, and the mixture was stirred for 30 min. After standing, the mixture was subjected to liquid separation, the insoluble substance in the organic layer was removed by filtration, and washed with 2-methyltetrahydrofuran (5.6 g). The filtrate and the washing were concentrated under reduced pressure. Addition of 2-methyltetrahydrofuran and concentration under reduced pressure were repeated twice. Addition of acetonitrile and concentration under reduced pressure were repeated twice to give a concentrated residue (0.64 g, crude yield 88%).

(HPLC purity (HPLC analysis condition 1): 69.0%.

Example 10 Synthesis of Compound [13]

At room temperature, compound [12A] (0.64 g, 1.6 mmol), compound [9] (0.21 g, 1.7 mmol) and acetonitrile (6.4 g) were charged, cesium carbonate (0.38 g, 1.2 mmol) was added thereto, and the mixture was warmed to 68° C., and stirred for 8 hr. The reaction mixture was cooled to room temperature, acetonitrile (6.4 g) was added thereto, and the mixture was concentrated under reduced pressure. To the concentrated residue were added toluene (12.8 g) and water (6.4 g), and the mixture was stirred at room temperature for 30 min. After standing, the mixture was subjected to liquid separation, tetrahydrofuran (6.4 g) and 3.8% aqueous sodium hydroxide solution (4.4 g, 4.2 mmol) were added to the organic layer, and the mixture was stirred for 19 hr. The reaction mixture was concentrated under reduced pressure, toluene (12.8 g) and water (6.4 g) were added thereto, and the mixture was stirred at room temperature for 30 min. After standing, the mixture was subjected to liquid separation, and the aqueous layer was adjusted to the pH to 1 to 2 with 3.5% hydrochloric acid (4.64 g). Toluene (12.8 g) was added thereto, and the mixture was stirred at room temperature for 30 min. After standing, the mixture was subjected to liquid separation, the organic layer was concentrated under reduced pressure to give a concentrated residue (0.44 g, yield 85%).

(HPLC purity (HPLC analysis condition 1): 75.6%.
LC-MS (APCI) [M+H]$^+$ 317
$^1$HNMR (400 MHZ, DMSO-$d_6$) δ12.52 (s, br, 1H), 8.18 (s, 1H), 7.40 (dd, J=14.4, 8.0 Hz, 1H), 7.29-7.23 (m, 2H), 7.13-7.08 (m, 1H), 4.64 (d, J=10.0 Hz, 1H), 4.28 (d, J=10.4 Hz, 1H), 2.46 (s, 1H), 2.26 (s, 1H), 2.14-2.11 (m, 1H), 1.61-1.57 (m, 2H)

INDUSTRIAL APPLICABILITY

According to the present invention, the objective (1R,2S)-2-{[((2,4-dimethylpyrimidin-5-yl)oxy}methyl]-2-(3-fluorophenyl)-N-(5-fluoropyridin-2-yl)cyclopropane-1-carboxamide (compound [A]) can be produced by an industrially advantageous method, i.e., using inexpensive compound [1] as a raw material, in a shorter process via a novel compound.

The invention claimed is:
1. A method of selectively producing an optically active compound represented by the formula [2]

[2]

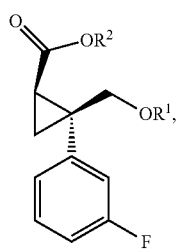

wherein R$^1$ is an alkylcarbonyl group, and R$^2$ is an alkyl group, the method comprising:

reacting a compound represented by the formula [1]

[1]

wherein R$^1$ is an alkylcarbonyl group, with an alkyl diazoacetate in the presence of copper trifluoromethanesulfonate and an optically active compound represented by the formula [5] or formula [6]

[5]

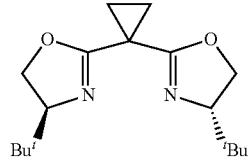

[6]

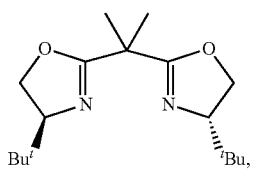

wherein $^t$Bu is a tert-butyl group, in an organic solvent.

2. A method of producing an optically active compound represented by the formula [4]

[4]

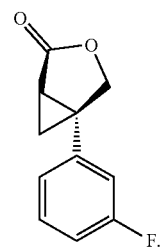

the method comprising:
selectively producing an optically active compound represented by the formula [2] by the method of claim 1,

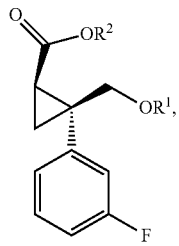

[2]

wherein R¹ is an alkylcarbonyl group, and R² is an alkyl group;
subjecting the optically active compound represented by the formula [2] to alkaline hydrolysis to produce an optically active compound represented by the formula [3]

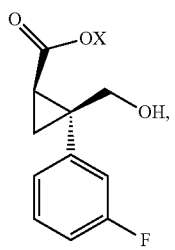

[3]

wherein X is an alkali metal; and
subjecting the optically active compound represented by the formula [3] to a cyclization reaction, thereby producing the optically active compound represented by the formula [4].

3. A method of producing an optically active compound represented by the formula [4]

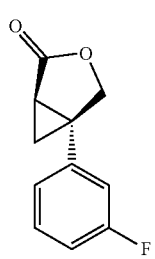

[4]

the method comprising:
reacting a compound represented by the formula [1]

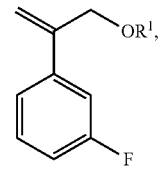

[1]

wherein R¹ is an alkylcarbonyl group,
with an alkyl diazoacetate in the presence of copper trifluoromethanesulfonate and an optically active compound represented by the formula [5] or formula [6]

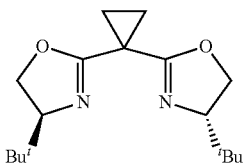

[5]

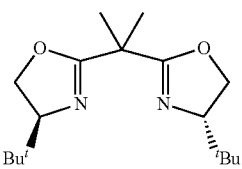

[6]

wherein $^t$Bu is a tert-butyl group,
in an organic solvent to produce a mixture comprising an optically active compound represented by the formula [2]

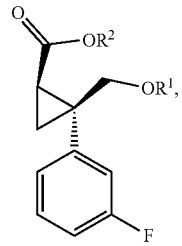

[2]

wherein R² is an alkyl group, and R¹ is an alkylcarbonyl group,
and an optically active compound represented by the formula [2a]

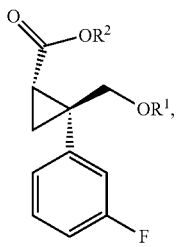

[2a]

wherein R¹ is an alkylcarbonyl group and R² is an alkyl group;

subjecting the mixture comprising the optically active compound represented by the formula [2] and the optically active compound represented by the formula [2a] to alkaline hydrolysis to produce a mixture comprising an optically active compound represented by the formula [3]

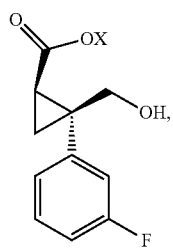

[3]

wherein X is an alkali metal, and an optically active compound represented by the formula [3a]

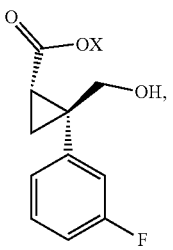

[3a]

wherein X is an alkali metal;

subjecting the optically active compound represented by the formula [3] to cyclization by adjusting the mixture comprising the optically active compound represented by the formula [3] and the optically active compound represented by the formula [3a] to pH 7.0 or lower with an acid to produce a mixture comprising an optically active compound represented by the formula [4]

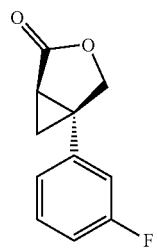

[4]

and an optically active compound represented by the formula [3b]

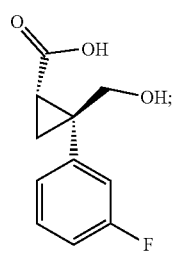

[3b]

and subjecting the mixture comprising the optically active compound represented by the formula [4] and the optically active compound represented by the formula [3b] to an extraction operation with an aromatic hydrocarbon solvent and a liquid separation operation to remove the optically active compound represented by the formula [3b] from the mixture comprising the optically active compound represented by the formula [4] and the optically active compound represented by the formula [3b].

4. The method according to claim 1, wherein the reacting of the compound represented by the formula [1] with the alkyl diazoacetate is carried out in the presence of copper trifluoromethanesulfonate and an optically active compound represented by the formula [5].

5. The method according to claim 3, further comprising washing the mixture comprising the optically active compound represented by the formula [3] and the optically active compound represented by the formula [3a] with an aromatic hydrocarbon solvent, and then removing the organic layer.

6. The method according to claim 3, wherein the mixture comprising the optically active compound represented by the formula [4] and the optically active compound represented by the formula [3b] is adjusted to pH 6.0 to 8.0, before the extraction operation with an aromatic hydrocarbon solvent and the liquid separation operation.

* * * * *